US006645524B2

(12) United States Patent
Midha et al.

(10) Patent No.: US 6,645,524 B2
(45) Date of Patent: *Nov. 11, 2003

(54) ORAL PHARMACEUTICAL DOSAGE FORMS FOR PULSATILE DELIVERY OF AN ANTIARRHYTHMIC AGENT

(75) Inventors: Kamal K. Midha, Hamilton (BM); Mark Hirsh, Wellesley, MA (US); Whe-Yong Lo, Canton, MA (US)

(73) Assignee: Pierce Management LLC, Wellesley, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/929,838

(22) Filed: Aug. 14, 2001

(65) Prior Publication Data

US 2002/0098232 A1 Jul. 25, 2002

Related U.S. Application Data

(63) Continuation-in-part of application No. 09/639,584, filed on Aug. 14, 2000.

(51) Int. Cl.⁷ ............... A61K 9/56; A61K 9/60; A61K 9/48; A61K 9/20; A61K 9/16
(52) U.S. Cl. ............ 424/459; 424/451; 424/464; 424/490; 424/496; 424/497; 424/474; 424/465
(58) Field of Search ................. 424/459, 451, 424/464, 490, 476, 497, 474, 465

(56) References Cited

U.S. PATENT DOCUMENTS

| | | |
|---|---|---|
| 4,777,049 A | 10/1988 | Magruder et al. |
| 4,788,180 A | 11/1988 | Bloch |
| 4,794,111 A | 12/1988 | Posanski et al. |
| 4,801,460 A | 1/1989 | Goertz et al. |
| 4,814,182 A | 3/1989 | Graham et al. |
| 4,863,744 A | 9/1989 | Urquhart et al. |
| 5,011,692 A | 4/1991 | Fujioka et al. |
| 5,017,381 A | 5/1991 | Maruyama et al. |
| 5,089,526 A | 2/1992 | Simon et al. |
| 5,110,597 A | 5/1992 | Wong et al. |
| 5,209,746 A | 5/1993 | Balaban et al. |
| 5,213,808 A | 5/1993 | Bar-Shalom et al. |
| 5,226,902 A | 7/1993 | Bae et al. |
| 5,260,068 A | 11/1993 | Chen |
| 5,260,069 A | 11/1993 | Chen |
| 5,387,419 A | 2/1995 | Levy et al. |
| 5,425,950 A | 6/1995 | Dandiker et al. |
| 5,456,679 A | 10/1995 | Balaban et al. |
| 5,472,708 A | 12/1995 | Chen |
| 5,508,040 A | 4/1996 | Chen |
| 5,614,220 A | 3/1997 | Hirakawa et al. |
| 5,618,560 A | 4/1997 | Bar-Shalom et al. |
| 5,681,584 A | 10/1997 | Savastano et al. |
| 5,837,284 A | 11/1998 | Mehta et al. |
| 5,840,329 A | * 11/1998 | Bai ..................... 424/457 |
| 5,874,475 A | 2/1999 | Hester, Jr. et al. |
| 5,877,196 A | 3/1999 | Tomcufcik et al. |
| 5,914,134 A | 6/1999 | Sharma |
| 5,916,584 A | 6/1999 | O'Donoghue et al. |
| 5,969,017 A | 10/1999 | Lynch, Jr. et al. |
| 6,001,391 A | 12/1999 | Zeidler et al. |
| 6,083,991 A | 7/2000 | Bergeron, Jr. |

OTHER PUBLICATIONS

Physicians Desk Online, Amiodarone, Sotalol, and Dofetilide.*

* cited by examiner

Primary Examiner—Thurman K. Page
Assistant Examiner—Amy E Pulliam
(74) Attorney, Agent, or Firm—Dianne E. Reed; Shelley P. Eberle; Reed & Eberle LLP

(57) ABSTRACT

Novel pharmaceutical dosage forms provide for pulsatile delivery of an antiarrhythmic agent that releases the drug in spaced apart "pulses." The dosage forms are comprised of first, second and optional third dosage units, with each dosage unit having a different drug release profile. The dosage forms may comprise capsules housing compressed tablets or drug-containing beads, granules, or particles or may comprise a single tablet with the first, second and optional third dosage units incorporated therein, or a "coated core" dosage form. Methods of treatment using the pharmaceutical dosage forms are provided as well.

64 Claims, No Drawings

ORAL PHARMACEUTICAL DOSAGE FORMS FOR PULSATILE DELIVERY OF AN ANTIARRHYTHMIC AGENT

CROSS-REFERENCE TO RELATED APPLICATION

This is a continuation-in-part of U.S. Ser. No. 09/639,584, filed Aug. 14, 2000, the disclosure of which is incorporated by reference.

TECHNICAL FIELD

The present invention relates generally to drug delivery, and more specifically relates to novel pharmaceutical dosage forms that provide pulsatile delivery of an antiarrhythmic agent for optimal therapeutic response. The invention additionally relates to methods for administering an antiarrhythmic agent using the novel dosage forms.

BACKGROUND

Antiarrhythmic agents are employed to treat patients suffering from, inter alia, cardiac contractions that are too rapid, too slow or asynchronous. Generally, antiarrhythmic agents are classified according to the Vaughan Williams' classification. For example, beta adrenoreceptor-blocking agents are classified as "Class II" antiarrhythmic agents and potassium channel blocking agents are classified as "Class III" antiarrhythmic agents.

Sotalol, N-[4-[1-hydroxy-2-[(1-methylethyl)amino]ethylphenyl]methane-sulfonamide, is a nonselective beta-adrenoreceptor blocking (Vaughan Williams Class II) agent with additional Class III antiarrhythmic properties, i.e., the ability to prolong the duration of the action potential. Both of these pharmacological properties contribute to the antiarrhythmic efficacy of sotalol. These same properties, however, may also cause cardiac toxicity with bradyarrhythmias, hypotension and torsade de pointes episodes, particularly with excessive doses of sotalol. Both isomers, i.e., d- and l-sotalol, have similar Class III antiarrhythmic effects, while the l-isomer is responsible for virtually all beta-blocking activity. The racemic form, i.e., dl-sotalol, has both Class III antiarrhythmic and beta-blocking activities and has been marketed as a treatment of documented ventricular arrhythmias, atrial fibrillation and atrial flutter.

Sotalol hydrochloride is currently marketed in the United States by Berlex Laboratories in 80, 120, 160 and 240 mg tablets. To reduce the risks associated with sotalol therapy, the labeling recommends that treatment should be initiated with low doses (80 mg twice daily) administered in a monitored setting followed by a gradual dose increase to 120 to 160 mg twice daily. The drug can be given parenterally and is marketed for intravenous administration in several countries outside the United States.

The clinical pharmacokinetics of sotalol have been extensively studied. The drug is completely absorbed after oral ingestion on an empty stomach with time to maximum concentration occurring between about two to four hours following ingestion. When given with food, absorption is approximately 80%. After absorption, there is no significant presystemic metabolism, and the drug is completely bioavailable. Sotalol is not subject to many drug/drug interactions since sotalol exhibits negligible protein binding. The apparent volume of distribution of sotalol is two liters per kilogram of body weight. There is no major biotransformation of the drug after its absorption in the liver or other organs, and it is eliminated almost entirely (80–90%) by renal excretion as unchanged sotalol. Sotalol has a terminal elimination half-life of about 10 to 20 hours, and the drug's pharmacokinetics are unchanged with long-term administration. The usual antiarrhythmic dose of sotalol hydrochloride is 160 to 320 mg daily given in two or three doses. The clearance of sotalol is decreased in renal insufficiency and adjustment in the dosing interval or doses becomes necessary in kidney-compromised situations. The elderly may also experience decreased elimination of sotalol due to an age-related reduction in renal clearance.

To minimize the risks associated with sotalol therapy, patients are initiated on the drug at low doses, under close supervision, while monitoring both the degree of beta-blockade as well as electrocardiac activity. This approach generally requires patients to stay in the hospital for four days during which the pharmacodynamic response is closely supervised. In this way, the physician is assured that the patient is suitably stabilized with respect to ventricular arrhythmias or supraventricular arrhythmias such as arterial fibrillation and arterial flutter. After normal rhythm has been achieved, patients are discharged with a view to continuing treatment with twice or three times daily administration of sotalol. In order to overcome compliance problems and assist caregivers, there is a need in the art for a dosage regimen wherein the drug is administered in a convenient dosage form, e.g., a dosage form administered once daily, to these critical patients. The present invention is addressed to this need in the art by providing a means for administering an antiarrhythmic drug, e.g., sotalol or dofetilide, in a convenient, once-a-day, dosage form for optimal response.

It has been reported that possible loss of clinical efficacy occurs as a result of pharmacological tolerance after twice or three times daily dosing (80 mg each administration) in four out of ten patients after six days of dosing. Padrini et al. (1997) Br. J. Clin. Pharmacol. 44:463–470; Le Coz (1992) Clin. Pharmacol. Ther. 52:417–426. Therefore, for optimal response and maintenance of efficacy in a majority of patients, it is important for patients to have a drug release-free or nearly drug release-free period in order to allow receptors to return to their basal state. Thus, in order to minimize the development of tolerance, there is a need for a delivery system to deliver sotalol in a pulsatile manner having the appropriate drug release profile.

Clearly, the development of such a pulsatile delivery release system would be more desirable than a sustained release dosage form which generally delivers an active agent in a zero order release or at a constant rate. It is important to understand that if constant plasma levels (i.e., as provided by dosage forms having a zero order release or constant rate release) are delivered (or maintained) in these patients, there is the potentially serious problem of lost clinical efficacy as a result of supra sensitization, i.e., loss of repolarization of the cardioreceptors associated with beta-blockade and potassium channel blockade. In effect, these receptors get "tired" due to constant presence of the drug. Preferably, the cardioreceptors are given a period of time free from the presence of the drug so that the cardioreceptors may return to their normal state.

By providing a pulsatile delivery dosage form for administering sotalol, the invention mimics twice or three times daily dosing of sotalol. That is, the invention provides an immediate dose followed by one or more pulsatile doses several hours after ingestion of the dosage form. The pulsatile delivery dosage form of the invention improves compliance in critically ill patients and minimizes the development of tolerance relative to a sustained release dosage form.

In addition, the pulsatile delivery dosage forms are ideal for controlling life-threatening arrhythmias in patients who have been discharged from clinical/hospital care.

A four-year Electrophysiologic Study vs. Electrocardiographic Monitoring (ESVEM) investigators' trial with sotalol has demonstrated that sotalol reduces the probability of recurrent ventricular tachycardia compared with Class I agents examined in the study. Lazzara et al. (1994) *Pacing Clin. Electrophysiol.* 17:473–477. This trial assessed the long-term efficacy of racemic sotalol, imipramine, mexiletine, pirmenol, procainamide, propafenone and quinidine in 496 patients with histories of sustained ventricular tachyarrhythmias who were identified as responders based upon electrophysiologic testing or Holter monitoring. In the ESVEM trial, sotalol was more effective than the other agents in preventing death from arrhythmias or any other cardiac cause.

Sotalol is associated with side effects of beta-adrenergic blocking agents with a 4 to 6% incidence of proarrhythmias and a general incidence of torsade de pointes episodes. The incidence of torsade de pointes episodes associated with sotalol administration is greatest in patients with a history of sustained ventricular tachycardia. It is common that most torsade de pointes episodes occur within three days upon starting the therapy and the risk is related to the dose. This risk increases at dosages above 320 mg per day. This is probably due to the fact that sotalol blocks potassium ion conductance in a concentration-related manner: the higher the concentration, the greater the potassium channel blockade and the duration of the ventricular action potential, i.e., the QT interval. Due to this relationship, the occurrence of torsade de pointes episodes associated with sotalol administration would appear to be predictable since concentration of sotalol can be monitored and pharmacodynamic response determined before initiating long-term therapy with the drug. Sotalol-induced proarrhythmias may be explained, at least in part, by the fact that nearly any drug that delays repolarization can result in early after-depolarizations. These are small membrane oscillations that occur before full cell recovery and they have been closely linked with torsade de pointes episodes.

From the SWORD trial (survival with oral d-sotalol, Waldo et al. (1995) *Am. J. Cardiol.* 75(15):1023–1027; Waldo et al. (1996) *Lancet* 348(9019):7–12) it is important to distinguish between racemic sotalol and d-sotalol, which has the pure potassium channel blocking activity. In this study of 3,121 high-risk post-myocardial infarction patients, who had a left ventricular ejection fraction of 40% or below, administration of d-sotalol was associated with presumed proarrhythmias and resulted in increased mortality compared with placebo. Therefore, it can be postulated that the strikingly different results of the SWORD and ESVEM trials may be related to the beta-adrenergic blocking activity of racemic sotalol. Similarly, it is possible that antiadrenergic modulation of prolonged repolarization may produce a beneficial effect that exceeds that of beta-blockade alone.

It has been suggested that sotalol plasma concentration associated with beta-blockade is four- to nine-fold lower than the plasma concentration associated with significant Class III actions. Wang et. al. (1986) *Am. J. Cardiol.* 57:1160–1165; Nattel et al. (1989) *J. Am. Coll. Cardiol.* 13:1190–1194. Other studies have shown, however, that the concentration of sotalol associated with Class II action (beta-blockade) is similar to those concentrations associated with minimal Class III action (potassium channel blockade).

The decrease in heart rate observed during treatment with sotalol may be explained by its beta-blocking (Class II) activity. d-Sotalol, which has very low affinity (50-fold less than l-sotalol) for the beta-adrenergic receptor, also slows heart rate. However, this effect is less pronounced than racemic sotalol. A study by Funck-Brentano et al. (Funck-Brentano et al. (1990) *Brit. J. of Clin. Pharmacol.* 30:195–202) found that more than 99% enantiomerically pure d-sotalol, when given in tablets, decreased resting and exercise heart rate without altering blood pressure. Subsequently, it was also reported that this decrease in heart rate was not due solely to binding of d-sotalol to beta-adrenergic receptors (Ysuda et al. (1993) *Clin. Pharma. and Ther.* 53:436–442). These observations suggest that prolongation of the duration of the action potential in the sinus node is responsible for the effects of d-sotalol on heart rate. Thus, a Class III effect of sotalol in the sinus node may contribute to the decrease in heart rate associated with beta-blocking activity. The Class III actions of most potassium channel blockers are associated with positive inotropy. Tande et al. (1991) *J. of Cardiovasc. Pharmacol.* 18:687–695; Baskin et al. (1991) *J. of Cardiovasc. Pharmacol.* 18:406–414. This positive inotropy associated with the Class III actions of sotalol may be counterbalanced by the negative inotropic actions associated with its beta-blocking activity. Despite the fact that sotalol appears to be well tolerated in patients with impaired left ventricular ejection fraction (Singh et al. (1989) *American J. of Cardiology* 64:943–945), some reports indicate that sotalol has the potential to decrease ventricular contractility (Mahmarian et al. (1987) *Circulation* 76:324–331).

More recent studies such as the ESVEM and SWORD trials have led Bawman to postulate (Bawman (1997) *Pharmacotherapy Supplement* 17:768–769) that the antiadrenergic modulation of prolonged repolarization may produce a beneficial effect that exceeds that of beta-blockade alone. Therefore, both d- and l-isomers contribute to the beneficial effects of racemic sotalol in Class III antiarrhythmic efficacy. The combination of Class II and Class III actions probably gives sotalol a unique pharmacodynamic profile relative to other antiarrhythmic drugs. Recently, Ritchie et al. (Ritchie et al. (1998) *J. of Cardiovasc. Pharmacol.* 31:876–884) reported short-term myocardial uptake of d- and l-sotalol in humans in relation to hemodynamic and electrophysiologic effects. That study demonstrated that both the uptake and attainment of peak effects of sotalol are very rapid in humans, which are irrespective of the effect of coronary disease and in spite of the existence of content/effect/hysteresis. Ritchie et al. demonstrated that myocardial handling of sotalol is not stereoselective. This, together with the recent finding that d-sotalol induces increased mortality by arrhythmogenesis (Bawman (1997), supra), suggest that the clinical efficacy of d, l-sotalol depends critically on the maintenance of combined beta-adrenoreceptor (Class II) and potassium channel (Class III) blockade.

Thus, it appears that both isomers of sotalol are required for clinical efficacy of sotalol for treating ventricular tachyarrhythmias or arterial fibrillation or flutter. Furthermore, the pure d-sotalol isomer may find application where potassium channel blockade is required, and the l-isomer where beta-blockade is required. Although sotalol in the United States has been marketed for ventricular arrhythmias, the drug had found off-label use in treatment of supraventricular arrhythmias such as arterial fibrillation and arterial flutter (Pink Sheet May $3^{rd}$, 1999). Currently, however, sotalol is approved for this indication in the United States and is marketed as Betapace AF™ by Berlix Laboratories, Inc., Montville, N.J.

In a US multi-center, a placebo-controlled, double-blind, dose response study of 253 patients with symptomatic primary paroxymal atrial fibrillation/atrial flutter, three fixed dose levels of 80 mg, 120 mg, or 160 mg of sotalol given twice a day were compared. The same doses were given once daily in patients who had reduced creatinine clearance (40–60 mL/min.). Patients were not randomized due to differences in the patient's characteristics and disease states. In the studied population, 64% of patients were male and the mean age was 62 years. Structural heart disease was absent in 43% of the patients. Due to reduced creatinine clearance, 20% of the patients received the drug doses once-daily.

Sotalol was demonstrated to prolong the time to first symptomatic ECG-documented recurrence of atrial fibrillation/atrial flutter. The median time to recurrence was 27, 106, 229, 175 days for placebo, 80 mg, 120 mg, and 160 mg dose levels, respectively. Thus, sotalol reduced the risk of such recurrences at both 6 and 12 months. The 120 mg dose was more effective than the 80 mg, but the 160 mg dose level did not offer any additional benefit over 120 mg dose level. Discontinuation because of adverse events was related to dose. Six % of patients discontinued medication in the placebo group whereas 12%, 18%, and 29% of the patients discontinued from the 80, 120, and 160 mg sotalol dose levels.

In another placebo controlled, double blind, multi-center study of 6 months' duration, 232 patients with chronic atrial fibrillation/atrial flutter were titrated over a dose range of from 80 mg/day to 320 mg/day. In this study the patients had mean age of 65 years and there were 70% males. Forty nine percent of the patients had structural heart disease. At entry, all patients had chronic atrial fibrillation for more than two weeks, but less than one year. The mean duration of atrial fibrillation in this population was 4.1 months. The patients followed a well defined entry criteria.

After successful cardio version, patients were randomized to either placebo (n=114) or Sotalol (n=118) at a starting dose of 80 mg b.i.d. If the initial dose was not tolerated, it was reduced to 80 mg once daily, but if it was tolerated, it was increased to 160 mg b.i.d. During the maintenance period, 67% of the patients were on 160 mg b.i.d. and the remainder were on 80 mg once daily (17%) and 80 mg b.i.d. (16%). Median time to recurrence of ECG-documented atrial fibrillation in the sotalol group was more than 180 days as compared to the placebo group having 44 days. (Physician Desk Reference, 2001).

Le Coz et al. (1992), supra, reported that in 83% of cases, $QT_c$ (the interval of the ventricular action potential corrected for heart rate) duration during repeated oral administration of racemic sotalol was below the value predicted from single administration. Furthermore, Le Coz et al reported that in 21% of cases, the measured $QT_c$ fell outside the 95% confidence interval predicted for the $QT_c$ value. A study by Padrini et al. (Padrini et al. (1997) *Br. J. Clin. Pharmacol.* 44:463–470) in 10 patients evaluated the issue of tolerance to the repolarization effects of racemic sotalol during long term treatment. In this study, QT interval duration was evaluated after a single oral 160 mg sotalol dose and after 6 days multiple oral sotalol dosing (80 mg, twice daily in 9 patients and 80 mg three times daily in one patient). It was noted that QT prolongation was linearly correlated with racemic sotalol plasma concentrations. The maximum QT interval prolongation and peak plasma concentration obtained with acute and chronic drug administration were not significantly different. During maintenance treatment with sotalol, partial loss of repolarization effect occurred in four out of the ten patients, suggesting pharmacodynamic tolerance. However, in the remaining six patients no such pharmacologic tolerance was noted, suggesting that in the majority of patients, twice or three times daily dosing would be appropriate.

Dofetilide is an antiarrhythmic agent that exhibits Class III activity (Vaughan Williams Classification). Currently, this drug is generally administered at twice a day. Consequently, patients receiving dofetilide would benefit from a once daily formulation containing this drug.

Therefore, delivery systems based on a pulsatile delivery approach, as provided herein, are the most desirable for critically ill patients. A delivery system of sotalol or an antiarrhymic agent which releases the drug in such a way that a constant concentration of drug is maintained in systemic circulation will not be appropriate for therapy because there will be loss of efficacy due to pharmacodynamic tolerance. This invention addresses this and other needs in the art by providing a delivery system for administration of an antiarrhythmic agent such that an immediate release dose is followed by one or more pulsatile doses that are released hours later. One such dosage form provides pulsatile delivery of an antiarrhythmic agent that mimics a twice daily dosing regimen. Another such dosage form provides pulsatile delivery of an antiarrhythmic agent that mimics a three times a day dosing regimen.

SUMMARY OF THE INVENTION

Accordingly, it is a primary object of the invention to address the above-mentioned needs in the art by providing a pharmaceutical dosage form for pulsatile delivery of an antiarrhythmic agent. Although the active agent may be any antiarrhythmic agent, it is preferred that the agent has Class II or III antiarrhythmic activity. Preferred Class II antiarrhythmic agents are dl-sotalol, d-sotalol, l-sotalol, pharmacologically acceptable acid addition salts thereof and mixtures of any of the foregoing. Preferred Class III antiarrhythmic agents are amiodarone and dofetilide and pharmacologically acceptable acid addition salts thereof.

It is another object of the invention to provide a pharmaceutical dosage form that provides an initial rapid release of a therapeutically effective dose of an antiarrhythmic agent followed by so-called "delayed release" pulses such that a second and optional third delayed dose of the active agent is released from the dosage form. By incorporating both an immediate release dosage unit and one or more delayed release dosage units of the active agent, the dosage form mimics a multiple dosing profile without repeated dosing, i.e., with only a single administration in a day. For example, the dosage form provides a twice daily dosing profile when the dosage form contains both an immediate release dosage unit and a single delayed release dosage unit. Alternatively, the dosage form provides a three times daily dosing profile when the dosage form contains an immediate release dosage unit and two delayed release dosage units.

Thus, the invention provides a pulsatile release dosage form for treating conditions responsive to the administration of an antiarrhythmic agent, wherein the dosage form comprises an immediate release dosage unit, a delayed release dosage unit and an optional second delayed release dosage unit. The immediate release dosage unit comprises a first dose of an active agent that is released substantially immediately following oral administration of the dosage form to a patient. The delayed release dosage unit comprises a second dose of the active agent and a means for delaying release of the second dose until approximately 6 hours to less than 14 hours following oral administration of the dosage form. The second delayed release dosage unit, when present, comprises a third dose of the active agent and a means for delaying release of the third dose until at least 14 hours to approximately 18 hours following oral administration of the dosage form.

Each dosage form contains a therapeutically effective amount of active agent. For dosage forms that mimic the twice daily dosing profile, approximately 30 wt. % to 70 wt. %, preferably 40 wt. % to 60 wt. %, of the total amount of active agent in the dosage form is released in the initial pulse, and, correspondingly approximately 70 wt. % to 30 wt. %, preferably 60 wt. % to 40 wt. %, of the total amount of active agent in the dosage form is released in the second pulse. For dosage forms mimicking the twice daily dosing profile, the second pulse is preferably released approximately 8 hours to less than 14 hours, and most preferably approximately 10 hours to 12 hours, following administration.

For dosage forms mimicking the three times daily dosing profile, approximately 25 wt. % to 40 wt. % of the total amount of active agent in the dosage form is released in the initial pulse, and approximately 25 wt. % to 40 wt. % of the total amount of active agent in the dosage form is released in each of the second and third pulses. For dosage forms that mimic the three times daily dosing profile, release of the second pulse preferably takes place approximately 6 hours to 10 hours, and most preferably approximately 7 to 9 hours, following oral administration. Release of the third pulse occurs about 4 hours to about 8 hours following the second pulse, and is typically about 14 hours to approximately 18 hours following oral.

In one aspect, the invention provides a dosage form comprising a closed capsule housing at least two drug-containing dosage units. Each dosage unit comprises two or more compressed tablets, or may be comprised of a plurality of beads, granules or particles, providing that each dosage unit has a different drug release profile. The immediate release dosage unit releases drug substantially immediately following oral administration to provide an initial dose. The delayed release dosage unit releases drug approximately 6 hours to 14 hours following oral administration to provide a second dose. Finally, an optional second delayed release dosage unit releases drug about 4 hours to 8 hours following the release of the second dose, and is typically 14 hours to 18 hours following oral administration.

Another dosage form of the invention comprises a compressed tablet having a drug-containing immediate release dosage unit, a delayed release dosage unit and an optional second delayed release dosage unit. In this dosage form, the immediate release dosage unit comprises a plurality of beads, granules or particles that release drug substantially immediately following oral administration to provide an initial dose. The delayed release dosage unit comprises a plurality of coated beads or granules, which release drug approximately 6 hours to 14 hours following oral administration to provide a second dose. An optional second delayed release dosage unit comprises coated beads or granules that release drug about 4 to 8 hours following administration of the initial delayed release dose, typically 14 to 18 hours following oral administration. The beads or granules in the delayed release dosage unit(s) are coated with a bioerodible polymeric material. This coating prevents the drug from being released until the appropriate time, i.e., approximately 6 hours to less than 14 hours following oral administration for the delayed release dosage unit and at least 14 hours to approximately 18 hours following oral administration for the optional second delayed release dosage unit. In this dosage form the components may be admixed in the tablet or may be layered to form a laminated tablet.

Another dosage form of the invention is a tablet having a drug-containing immediate release dosage unit, a delayed release dosage unit, and an optional second delayed release dosage unit, wherein the immediate release dosage unit comprises an outer layer that releases the drug substantially immediately following oral administration. The arrangement of the remaining delayed release dosage(s), however, depends upon whether the dosage form is designed to mimic twice daily dosing or three times daily dosing.

In the dosage form mimicking twice daily dosing, the delayed release dosage unit comprises an inner core that is coated with a bioerodible polymeric material. The coating is applied such that release of the drug occurs approximately 6 hours to less than 14 hours following oral administration. In this form, the outer layer completely surrounds the inner core.

In the dosage form mimicking three times a day dosing, the (first) delayed release dose comprises an internal layer that releases drug approximately 6 hours to less than 14 hours following oral administration. This internal layer is surrounded by the outer layer. The second delayed release dosage unit generally comprises an inner core that releases the drug at least 14 hours to approximately 18 hours following oral administration. Thus, the layers of this tablet (starting from the external surface) comprise an outer layer, an internal layer and an inner core. The inner core comprises delayed release beads or granules. Furthermore, the internal layer comprises the drug coated with a bioerodible polymeric material.

Alternatively, in this particular dosage form mimicking three times a day dosing, both the delayed release dosage unit and second delayed release dosage units are surrounded by an inner layer. This inner layer is free of active agent. Thus, the layers of this tablet (starting from the external surface) comprise an outer layer, inner layer and an admixture of the delayed release dosage units. The first delayed release pulse occurs once the inner layer is substantially eroded thereby releasing the admixture of the delayed release dosage units. The dose corresponding to the (first) delayed release dosage unit is released immediately since the inner layer has prevented access to this dose for the appropriate time, e.g., from approximately 6 hours to 10 hours. The second delayed release dose, however, is formulated to effectively delay release for at least 14 hours to approximately 18 hours following oral administration.

For formulations mimicking twice daily dosing, it is preferred that the delayed release dose is released approximately 8 hours to less than 14 hours, most preferably approximately 10 hours to 12 hours, following oral administration. For formulations mimicking three times daily dosing, it is preferred that the (first) delayed release dose is released approximately 6 to 10 hours, preferably 7 hours to 9 hours, following oral administration. For dosage forms containing a third dose, the third dose (i.e., the second delayed release dose) is released at least 14 hours to approximately 18 hours following oral administration.

It is another object of the invention to provide methods for administering antiarrhythmic agents, e.g., d-sotalol, l-sotalol or combinations thereof (including d,l-sotalol, i.e., racemic sotalol), amiodarone, dofetilide, azimilide, cibenzoline, and bunafitidine, using the novel dosage forms.

The novel drug dosage forms are to be administered orally to a mammalian individual and can be used to administer an antiarrhythmic agent to treat or to prevent a variety of cardiovascular disorders, conditions and diseases. In accordance with the present invention, administration of the antiarrhythmic agent may be carried out in order to treat any disorder, condition or disease for which antiarrhythmic agents are generally indicated either now or in the future. Such cardiovascular conditions and diseases include, for example, documented ventricular arrhythmias (such as sustained ventricular tachycardia, which can be life threatening) and atrial fibrillation/atrial flutter.

DETAILED DESCRIPTION OF THE INVENTION

Before the present formulations and methods of use are disclosed and described, it is to be understood that unless otherwise indicated this invention is not limited to specific pharmacologically active agents, specific pharmaceutical carriers, or to particular administration regimens, as such may vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "an active agent" includes a single active agent as well as combinations of different active agents, reference to "a pharmaceutical carrier" includes a single pharmaceutical carrier as well as combinations of two or more carriers, reference to "a compressed tablet" includes a single as well as a plurality of compressed tablets, reference to "an immediate release dosage form" includes a single immediate release dosage form in addition to a group of two or more immediate release dosage forms, reference to "a coating" as in "a delayed release coating" includes a single coating as well as two or more coatings, and the like.

In this specification and in the claims which follow, reference will be made to a number of terms which shall be defined to have the following meanings:

"Optional" or "optionally" means that the subsequently described circumstance may or may not occur, so that the description includes instances where the circumstance occurs and instances where it does not. For example, when an "optional second delayed release dosage unit" appears in describing the dosage forms, "optional second delayed release dosage unit," means that the second delayed release dosage unit may or may not be present, and thus, the description includes dosage forms wherein the second delayed release dosage unit is present and dosage forms wherein the second delayed release dosage unit is not present.

The terms "active agent," "pharmacologically active agent" and "drug" are used interchangeably herein to refer to a chemical compound that induces a desired pharmacological, physiological effect, i.e., in this case, prevention or treatment of arrhythmia. The terms also encompass pharmaceutically acceptable, pharmacologically active derivatives of those active agents specifically mentioned herein, including, but not limited to, salts, esters, amides, prodrugs, active metabolites, analogs, and the like. When the terms "active agent," "pharmacologically active agent" and "drug" are used, then, or when a particular antiarrhythmic agent is specifically identified, it is to be understood that applicants intend to include the active agent per se as well as pharmaceutically acceptable, pharmacologically active salts, esters, amides, prodrugs, metabolites, analogs, etc.

By the terms "effective amount" or "pharmaceutically effective amount" of an agent as provided herein are meant a nontoxic but sufficient amount of the agent to provide the desired prophylactic or therapeutic effect. The exact amount required will vary from subject to subject, depending on age, general condition of the subject, the severity of the condition being treated, the particular active agent administered, and the like. Thus, it is not possible to specify an exact "effective amount." However, an appropriate "effective" amount in any individual case may be determined by one of ordinary skill in the art using routine experimentation.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Thus, for example, "treating" an arrhythmia, as the term is used herein, encompasses both prevention of the arrhythmia in predisposed individuals as well as treatment of arrhythmia in clinically symptomatic individuals.

By "pharmaceutically acceptable" carrier is meant a carrier comprised of a material that is not biologically or otherwise undesirable, i.e., the material may be administered to an individual along with the selected active agent without causing any undesirable biological effects or interacting in a deleterious manner with any of the other components of the pharmaceutical composition in which it is contained. The term "carrier" is used generically herein to refer to any components present in the pharmaceutical formulations other than the active agent or agents, and thus includes diluents, binders, lubricants, disintegrants, fillers, coloring agents, wetting or emulsifying agents, pH buffering agents, preservatives, and the like.

Similarly, a "pharmaceutically acceptable" salt of a compound as provided herein is a salt that is not biologically or otherwise undesirable.

The active agent incorporated in the "pulsatile release" dosage forms of the present invention is an antiarrhythmic agent. Antiarrhythmic agents include those agents that normalize irregular electrical activity of cardiac tissue. According to the Vaughan Williams' classification, antiarrhythmic agents are loosely classified in the following groups: Class I agents, exemplified by the sodium channel-blocking drugs; Class II agents, exemplified by beta adrenoreceptor-blocking agents; Class III agents, exemplified by drugs that prolong the effective refractory period by prolonging the action potential; and Class IV agents, exemplified by calcium channel-blocking agents.

The antiarrhythmic agent may be present in the formulation as a salt, ester, amide or other derivative, or may be functionalized in various ways as will be appreciated by those skilled in the art and described in the pertinent texts, patents and literature. The antiarrhythmic agents of the present invention can either be synthesized using techniques well known in the art or obtained from commercial suppliers.

The antiarrhythmic agent may be in the form of a salt, ester, amide, prodrug, derivative or the like, provided that the salt, ester, amide, prodrug or derivative is suitable pharmacologically, i.e., effective in treating cardiac arrhythmias. Salts esters, amides, prodrugs and other derivatives of the antiarrhythmic agents may be prepared using standing procedures known to those skilled in the art of synthetic organic chemistry and described, for example, by J. March, *Advanced Organic Chemistry: Reactions, Mechanisms and Structure*, 4th edition. (New York: Wiley-Interscience, 1992). For example, acid addition salts are prepared from the free base using conventional methodology, and involves reaction with a suitable acid. Generally, the base form of the drug is dissolved in a polar organic solvent such as methanol or ethanol and the acid is added thereto. The resulting salt either precipitates or may be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Particularly preferred acid addition salts of the antiarrhythmic agents herein are halide salts, such as may be prepared using hydrochloric or hydrobromic acids. Conversely, preparation of basic salts of acid moieties which may be present on the molecule of the antiarrhythmic agent are prepared in a similar manner using a pharmaceutically acceptable base such as sodium hydroxide, potassium hydroxide, ammonium hydroxide, calcium hydroxide, trimethylamine, or the like. Particularly preferred basic salts herein are alkali metal salts, e.g., sodium salt, and copper salts. Preparation of esters involves functionalization of hydroxyl and/or carboxyl groups which may be present within the molecular structure of the drug. The esters are typically acyl-substituted derivatives of free alcohol groups, i.e., moieties which are derived from carboxylic acids of the formula RCOOH where R is alkyl, and preferably is lower alkyl. Esters can be reconverted to the free acids, if desired, by using conventional hydrogenolysis or hydrolysis procedures. Amides and prodrugs may also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine. Prodrugs are typically prepared by covalent attachment of a moiety which results in a compound that is therapeutically inactive until modified by an individual's metabolic system. Preferred compounds are in salt form, such as the acid addition (e.g., HCl) salts of sotalol and amiodarone.

Stereoisomers of the active agents are also included as part of the dosage forms described herein. A stereoisomer is a compound having the same molecular weight, chemical composition, and constitution as another, but with the atoms arranged differently. That is, certain identical chemical moieties are at different orientations in space. This difference has the consequence of rotating the plane of polarized light. A pair of stereoisomers that are mirror images of each other are defined as enantiomers. Individual stereoisomers or enantiomers may have unique or beneficial properties that make that individual isomer particularly well-suited for the present invention. Consequently, individual stereoisomers or enantiomers and mixtures thereof of the active agents are included as part of the invention. Thus, each active agent may be present in the formulation as a racemate, i.e., equal amounts of each enantiomer, an enantiomerically pure form, e.g., d-sotalol, l-sotalol, or a mixture of nonequal amounts of each enantiomer, e.g., nonequal amounts of d-sotalol/l-sotalol.

Although any antiarrhythmic agent can be included in the invention, preferred active agents are d-sotalol, l-sotalol or combinations thereof (including d,l-sotalol, i.e., racemic sotalol), amiodarone, dofetilide, azimilide, cibenzoline, and bunaftitidine. Although any form (e.g., salt, base or amide form) may be used, a salt form is preferred with sotalol and amiodarone. A particularly preferred active agent herein is sotalol hydrochloride, including d-sotalol hydrochloride, l-sotalol hydrochloride, and d,l-sotalol hydrochloride.

The invention provides pharmaceutical dosage forms that provide the pulsatile delivery of an antiarrhythmic agent. By "pulsatile" is meant that a plurality of drug doses are released at spaced apart intervals of time. Generally, upon ingestion of the dosage form, release of the initial dose is substantially immediate, i.e., the first drug release "pulse" occurs within about one hour of ingestion. This initial pulse is followed by a first time interval during which very little or no drug is released from the dosage form, after which a second dose is then released. Similarly, a second nearly drug release-free interval between the second and third drug release pulses may be designed. The duration of the nearly drug release-free time interval will vary depending upon the dosage form design e.g., a twice daily dosing profile, a three times daily dosing profile, etc. For dosage forms providing a twice daily dosage profile, the nearly drug release-free interval has a duration of approximately 8 hours to 12 hours between the first and second dose. For dosage forms providing a three times daily profile, the nearly drug release-free interval has a duration of approximately 7 hours to 9 hours between each of the three doses.

In one embodiment, the aforementioned pulsatile release profile is achieved with dosage forms that are closed and preferably sealed capsules housing at least two drug-containing "dosage units" wherein each dosage unit within the capsule provides a different drug release profile. Control of the delayed release dosage unit(s) is accomplished by a controlled release polymer coating on the dosage unit, or by incorporation of the active agent in a controlled release polymer matrix. Each dosage unit may comprise a compressed or molded tablet, wherein each tablet within the capsule provides a different drug release profile. For dosage forms mimicking a twice a day dosing profile, a first tablet releases drug substantially immediately following ingestion of the dosage form, while a second tablet releases drug approximately 6 hours to less than 14 hours following ingestion of the dosage form. For dosage forms mimicking a three times daily dosing profile, a first tablet releases drug substantially immediately following ingestion of the dosage form, a second tablet releases drug approximately 6 hours to less than 14 hours following ingestion of the dosage form, and the third tablet releases drug at least 14 hours to approximately 18 hours following ingestion of the dosage form. It is possible that the dosage form includes more than three tablets. While the dosage form will not generally include more than a third tablet, dosage forms housing more than three tablets are within the scope of the present invention.

Alternatively, each dosage unit in the capsule may comprise a plurality of drug-containing beads, granules or particles. As is known in the art, drug-containing "beads" refer to beads made with drug and one or more excipients or polymers. Drug-containing beads can be produced by applying drug to an inert support, e.g., inert sugar beads coated with drug or by creating a "core" comprising both drug and one or more excipients. As is also known, drug-containing "granules" and "particles" comprise drug particles that may or may not include one or more additional excipients or polymers. In contrast to drug-containing beads, granules and particles do not contain an inert support. Granules generally comprise drug particles and require further processing. Generally, particles are smaller than granules, and are not further processed. Although beads, granules and particles may be formulated to provide immediate release, beads and granules are generally employed to provide delayed release.

For dosage forms mimicking a twice a day dosing profile, a first group beads, granules or particles releases drug substantially immediately following ingestion of the dosage form, while a second group of beads or granules preferably releases drug approximately 8 hours to less than 14 hours following ingestion of the dosage form. For dosage forms mimicking a three times daily dosing profile, a first group of beads, granules or particles releases drug substantially immediately following ingestion of the dosage form, a second group of beads or granules preferably releases drug approximately 6 hours to 10 hours following ingestion of the dosage form, and a third group of beads, granules or particles releases drug at least 14 hours to approximately 18 hours following ingestion of the dosage form. The above-mentioned tablets, beads, granules and particles of different drug release profiles (e.g., immediate and delayed release profiles) may be mixed and included in a capsule to provide a pulsatile dosage form having the desired release profile.

In another embodiment, the individual dosage units are compacted in a single tablet, and may represent integral but discrete segments thereof (e.g., layers), or may be present as a simple admixture. For example, drug-containing beads, granules or particles with different drug release profiles (e.g., immediate and delayed release profiles) can be compressed together into a single tablet using conventional tableting means.

In a further alternative embodiment, a dosage form is provided that comprises an inner drug-containing core and at least one drug-containing layer surrounding the inner core. An outer layer of this dosage form contains an initial, immediate release dose of the drug. For dosage forms mimicking twice daily dosing, the dosage form has an outer layer that releases drug substantially immediately following oral administration and an inner core having a polymeric-coating that preferably releases the active agent approximately 8 hours to less than 14 hours following ingestion of the dosage unit. For dosage forms mimicking three times daily dosing, the dosage form has an outer layer that releases drug substantially immediately following oral administration, an inner core that preferably releases drug at least 14 hours to 18 hours following oral administration and a layer interposed between the inner core and outer layer that preferably releases drug approximately 6 hours to 10 hours following ingestion of the dosage form. The inner core of the dosage form mimicking three times daily a dosing may be formulated as compressed delayed release beads or granules.

Alternatively, for dosage forms mimicking three times daily dosing, the dosage form has an outer layer and an inner layer free of drug. The outer layer releases drug substantially immediately following oral administration, and completely surrounds the inner layer. The inner layer surrounds both the second and third doses and preferably prevents release of these doses for approximately 6 hours to 10 hours following oral administration. Once released, the second dose is immediately available while the third dose is formulated as delayed release beads or granules such that release of the third dose is effected approximately 4 hours to 12 thereafter effectively resulting in release of the third dose at least 14 hours to approximately 18 hours following ingestion of the dosage form. The second and third doses may be formulated by admixing immediate release and delayed release beads, granules or particles and compressing the admixture to form a second and third dose-containing core followed by polymeric coating to achieve the desired three times daily dosing profile.

In still another embodiment, a dosage form of the invention comprises a coated core-type delivery system wherein the outer layer is comprised of an immediate release dosage unit, such that active agent therein is immediately release following oral administration, an intermediate layer thereunder surrounds a core, and the core is comprised of immediate release beads or granules and delayed release beads or granules, such that the second dose is provided by the immediate release beads or granules and the third dose is provided by the delayed release beads or granules.

As will be appreciated by those skilled in the art and as described in the pertinent texts and literature, a number of methods are available for preparing drug-containing tablets, beads, granules or particles that provide a variety of drug release profiles. Such methods include, but are not limited to, the following: coating a drug or drug-containing composition with an appropriate coating material, typically although not necessarily a incorporating a polymeric material; increasing drug particle size; placing the drug within a matrix; and forming complexes of the drug with a suitable complexing agent.

The delayed release dosage units in any of the above embodiments can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials are comprised of bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. Generally, however, a coating weight of approximately 5 wt. % to 50 wt. % is used to achieve an approximately 6 hour to less than 14 hour delay in release of the active agent. Additional amounts of the coating material will provide longer delays in release, e.g., at least a 14 hour to approximately 18 hour delay in release.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers are, but not limited to, polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

The delayed release dosage units may be coated with the delayed release polymer coating using conventional techniques, e.g., using a conventional coating pan, an airless spray technique, fluidized bed coating equipment (with or without a Wurster insert), or the like. For detailed information concerning materials, equipment and processes for preparing tablets and delayed release dosage, reference may be made to *Pharmaceutical Dosage Forms: Tablets*, eds. Lieberman et al. (New York: Marcel Dekker, Inc., 1989), and to Ansel et al., *Pharmaceutical Dosage Forms and Drug Delivery Systems*, $6^{th}$ Ed. (Media, Pa: Williams & Wilkins, 1995).

Alternatively, a delayed release tablet may be formulated by dispersing the drug within a matrix of a suitable material such as a hydrophilic polymer or a fatty compound. The hydrophilic polymers may be comprised of polymers or copolymers of cellulose, cellulose ester, acrylic acid, methacrylic acid, methyl acrylate, ethyl acrylate, and vinyl or enzymatically degradable polymers or copolymers as described above. These hydrophilic polymers are particularly useful for providing a delayed release matrix. Fatty compounds for use as a matrix material include, but are not limited to, waxes (e.g. carnauba wax) and glycerol tristearate. Once the active ingredient is mixed with the matrix material, the mixture can be compressed into tablets.

The immediate release dosage unit of the dosage form—i.e., a tablet, a plurality of drug-containing beads, granules or particles, or an outer layer of a coated core dosage form—contains a therapeutically effective quantity of the active agent with conventional pharmaceutical excipients. The immediate release dosage unit may or may not be coated, and may or may not be admixed with the delayed release dosage unit or units (as in an encapsulated mixture of immediate release drug-containing granules, particles or beads and delayed release drug-containing granules or beads). A preferred method for preparing immediate release tablets (e.g., as incorporated into a capsule) is by compressing a drug-containing blend, e.g., blend of granules, prepared using a direct blend, wet-granulation or dry-granulation process. Immediate release tablets may also be molded rather than compressed, starting with a moist material containing a suitable water-soluble lubricant. However, preferred tablets herein are manufactured using compression rather than molding. A preferred method for forming immediate release drug-containing blend is to mix drug particles directly with one or more excipients such as diluents (or fillers), binders, disintegrants, lubricants, glidants, colorants or the like. As an alternative to direct blending, a drug-containing blend may be prepared by using a wet-granulation or dry-granulation processes. Beads containing the active agent may also be prepared by any one of a number of conventional techniques, typically starting from a fluid dispersion. For example, a typical method for preparing drug-containing beads involves blending the active agent with conventional pharmaceutical excipients such as microcrystalline cellulose, starch, polyvinylpyrrolidone, methylcellulose, talc, metallic stearates, silicone dioxide, or the like. The admixture is used to coat a bead core such as a sugar sphere (or so-called "non-pareil") having a size of approximately 20 to 60 mesh.

An alternative procedure for preparing drug beads is by blending drug with one or more pharmaceutically acceptable excipients, such as microcrystalline cellulose, lactose, cellulose, polyvinyl pyrrolidone, talc, magnesium stearate, a disintegrant, etc., extruding the blend, spheronizing the extrudate, drying and optionally coating to form the immediate release beads.

Optional pharmaceutically acceptable excipients present in the drug-containing tablets, beads, granules or particles include, but are not limited to, diluents, binders, lubricants, disintegrants, colorants, stabilizers, surfactants and the like. Diluents, also termed "fillers," are typically necessary to increase the bulk of a solid dosage form so that a practical size is provided for compression of tablets or formation of beads and granules. Suitable diluents include, for example, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powder sugar. Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone. Lubricants are used to facilitate tablet manufacture; examples of suitable lubricants include, for example, magnesium stearate, calcium stearate, stearic acid, glycerol behenate, and polyethylene glycol, talc, and mineral oil. Disintegrants are used to facilitate dosage form disintegration or "breakup" after administration, and are generally starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp). Stabilizers are used to inhibit or retard drug decomposition reactions which include, by way or example, oxidative reactions. Surfactants may be anionic, cationic, amphoteric or nonionic surface active agents. Suitable anionic surfactants include, but not limited to those containing carboxylate, sulfonate and sulfate ions. Examples for anionic surfactants are sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but not limited quaternary ammonium compounds such as benzalkonium chloride, benzethonium chloride, cetrimonium bromide, stearyl dimethylbenzyl ammonium chloride, polyoxyethylene (15) and coconut amine. Examples for nonionic surfactants are, but not limited to, ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene (8) monolaurate, polysorbates, polyoxyethylene (9) octylphenylether, PEG-1000 cetyl ether, polyoxyethylene (3) tridecyl ether, polypropylene glycol (18) butyl ether, Poloxamer 401, stearoyl monoisopropanolamide, and polyoxyethylene (5) hydrogenated tallow amide. Examples for amphoteric surfactants are, but not limited to, sodium N-dodecyl-β-alanine, sodium N-lauryl-β-iminodipropionate, myristoamphoacetate, lauryl betaine and lauryl sulfobetaine. If desired, the tablets, beads granules or particles may also contain minor amount of nontoxic auxiliary substances such as wetting or emulsifying agents, pH buffering agents, preservatives, and the like.

The amount of active agent released in each dose will be a therapeutically effective amount, and will depend upon the dosage form itself (e.g., a dosage form having a twice daily dosing profile). When sotalol is included in the dosage form, the total amount of sotalol or a pharmaceutically acceptable salt thereof (e.g., the hydrochloride salt) in the dosage unit is in the range of approximately 50 mg to 700 mg, preferably 80 mg to 640 mg. When amiodarone is included in the dosage form, the total amount of amiodarone or a pharmaceutically acceptable salt thereof (e.g., the hydrochloride salt) in the dosage unit is in the range of approximately 200 mg to 1000 mg, preferably 400 mg to 800 mg. When dofetilide is included in the dosage form, the total amount of dofetilide contained in the immediate release, delayed release and optional second delayed release dosage units is in the range of approximately 10 μg to 10 mg, preferably about 200 μg to 1000 μg, such that in a b.i.d. dosage form, each dosage unit comprises about 5 μg to 5 mg, preferably about 100 μg to 500 μg, and in a t.i.d. dosage form, each dosage unit comprises approximately 3.33 μg to 3.33 mg, preferably about 66.7 μg to 333 μg.

Typically, the total amount of active agent in a dosage form is divided evenly between each pulse contained in the dosage form. For dosage forms that mimic a twice a day profile, the active agent in immediate release form generally represents about 30 wt. % to 70 wt. %, preferably 40 wt. % to 60 wt. %, of the total active agent in one dosage form, while, correspondingly, the active agent in the delayed release form generally represents about 70 wt. % to 30 wt. %, preferably 60 wt. % to 40 wt. %, of the total active agent in one dosage form. Similarly, for dosage forms that mimic three times daily dosing profile, the active agent in the immediate release unit(s) and in each of the two delayed release units represents about 20 wt. % to 50 wt. %, preferably 25 wt. % to 40 wt. %, of the total active agent in one dosage form.

For dosage forms containing sotalol and mimicking a twice daily dosing profile, the immediate release dosage unit typically contains approximately 25 mg to 350 mg, preferably about 40 mg to 320 mg, of sotalol while the delayed release dosage unit correspondingly contains approximately 350 mg to 25 mg, preferably about 320 mg to about 40 mg, such that the total daily dose is generally in the range of approximately 50 mg to about 700 mg, preferably about 80 mg to about 640 mg.

For a three-pulse dosage form for administration of sotalol, the immediate release dosage unit in each dosage form typically contains approximately 16 mg to 233 mg, preferably 26 mg to 214 mg, of sotalol while each of the delayed release dosage units correspondingly contains approximately 233 mg to 16 mg, preferably 214 mg to 26 mg, of the active agent.

For dosage forms containing amiodarone and mimicking a twice daily dosing profile, the immediate release dosage unit typically contains approximately 200 to 600 mg, preferably about 250 mg to 550 mg, most preferably about 300 mg to 400 mg of amiodarone, while the delayed release dosage unit contains, correspondingly, approximately 600 mg to 200 mg, preferably about 550 mg to 250 mg, most preferably about 400 mg to 300 mg amiodarone, such that the total daily dose is in the range of about 600 to 800 mg.

The invention also includes a method for treating an individual suffering from a cardiac arrhythmia comprising orally administering a dosage form of the invention preferably, although not necessarily, once daily. Typically the dosage forms are employed to treat individuals suffering from atrial fibrillation, atrial flutter, supra ventricular arrhythmia, ventricular tachycardia (including sustained ventricular tachycardia) and ventricular arrhythmia. By providing pulsatile release of the active agent, the dosage forms of the invention minimize the development of tolerance (and thereby loss of efficacy) due to supersensitization of the cardioreceptors.

It is to be understood that while the invention has been described in conjunction with the preferred specific embodiments thereof, that the description above as well as the examples that follow are intended to illustrate and not limit the scope of the invention. Other aspects, advantages and modifications within the scope of the invention will be apparent to those skilled in the art to which the invention pertains.

All patents, patent applications and publications mentioned herein are incorporated by reference in their entireties.

Experimental:

The practice of the present invention will employ, unless otherwise indicated, conventional techniques of pharmaceutical formulation, medicinal chemistry, biological testing, and the like, which are within the skill of the art. Such techniques are explained fully in the literature. Preparation of various types of pharmaceutical formulations are described, for example, in Lieberman et al., cited supra; synthesis of chiral drugs is described, inter alia, in Wilson and Grisvold, *Textbook of Organic, Medicinal and Pharmaceutical Chemistry* (Lippincott-Raven Publishers, 1991); and Gibaldi and Perrier, *Pharmacokinetics* (Marcel Dekker, 1982), provides a description of the biological testing procedures useful to evaluate compounds such as those described and claimed herein. In the following examples, efforts have been made to ensure accuracy with respect to

EXAMPLE 1

Preparation of Immediate Release Granulation

An immediate release granulation of sotalol hydrochloride is prepared using the components of Table 1:

TABLE 1

| COMPONENT | AMOUNT w/w % | PREFERRED AMOUNT w/w % |
|---|---|---|
| Sotalol hydrochloride | 50–90 | 60–80 |
| Sodium starch glycolate | 0–10 | 2–8 |
| Filler (Lactose or/and Microcrystalline cellulose) | 5–50 | 10–30 |
| Starch | 5–20 | 7–15 |
| Magnesium stearate | 0.2–1.0 | 0.3–0.8 |
| Silicon dioxide | 0.2–1.0 | 0.3–0.8 |
| Optional colorant | 0.5–5 | 0.5–2 |

The blend is prepared by mixing 5 kg sotalol hydrochloride powder, 1 kg microcrystalline cellulose or lactose or combination thereof and 800 g starch in a granulating bowl. The powder blend is then granulated with water to form a wet mass. The wet granules are dried in a conventional oven or in a fluid bed dryer until the moisture content is less than 5%. The dried granulation is milled using a conventional pharmaceutical mill or screened through a 16 to 20 mesh. The resulting screened granulation is blended with 300 g sodium starch glycolate, 40 g magnesium stearate and 40 g silicone dioxide.

EXAMPLE 2

Preparation of Immediate Release Tablet Cores

The granulation blend prepared in Example 1 may be compressed into tablets using conventional tableting equipment. The desired tablet weight is approximately 50 mg to 525 mg, which provides 40 to 360 mg sotalol hydrochloride in one tablet. Tablets having a diameter in the range of approximately 1/16 to 1/2 inches are optimal.

EXAMPLE 3

Preparation of Immediate Release Bead Cores

A sotalol hydrochloride blend is prepared by blending 10 kg sotalol hydrochloride and 1 kg talc for 15 minutes and the admixture is screened or milled using a suitable mesh sieve to obtain a homogenous fine powder. Then, a 10% w/w solution of polyvinylpyrrolidone in ethanol or water is prepared as a binding solution. A coating pan is then loaded with 10 kg of inert sugar spheres (20 to 50 mesh). The sugar spheres are sprayed with the binding solution and the sotalol blend is applied to the sugar spheres. Talc may be used to dust the beads. The coating process is continued until the desired amount of sotalol is exhausted. The resulting bead cores are dried to remove solvent.

EXAMPLE 4

Preparation of Immediate Release Bead Cores

Polyvinylpyrrolidone (500 g) is dissolved in about 25 kg water (or a mixture of water and alcohol) and 10 kg of sotalol hydrochloride is mixed therein to provide a sotalol/binder solution. In a fluidized bed coater, 10 kg of sugar spheres (20 to 50 mesh) are suspended in warm air and spray coated with the sotalol/binder solution until the seeds are uniformly coated with a desired amount of sotalol.

EXAMPLE 5

Preparation of Immediate Release Bead Cores

Sotalol hydrochloride (10 kg) and 10 kg of microcrystalline cellulose are blended to form a uniform blend. Approximately 10 to 15 kg water is added slowly to the blend and mixed. The resulting granulate is extruded at high speed through a plate (e.g., a 1.0 mm plate) and spheronized using an extruder/spheronizer. The spheres are then dried to a moisture content of less than 7%.

EXAMPLE 6

Preparation of Immediate Release Bead Cores

Sotalol hydrochloride (10 kg), 6 kg of microcrystalline cellulose, 0.5 kg methylcellulose and 0.4 kg sodium starch glycolate are blended to form a uniform blend. About 10 kg water is added slowly and the blend is mixed. The resulting granulate is extruded at high speed through a plate (e.g., a 1.0 mm plate) and spheronized using a extruder/spheronizer. The spheres are then dried to a moisture content of less than 7%.

EXAMPLE 7

Preparation of Immediate Release Bead Cores

Sotalol hydrochloride (10 kg), 6 kg of microcrystalline cellulose, 2 kg glycerol monostearate are blended to form a uniform blend. About 10 kg water is added slowly and the blend is mixed. The resulting granulate is extruded at high speed through a plate (e.g., a 1.0 mm plate) and spheronized using a extruder/spheronizer. The spheres are then dried to a moisture content of less than 7%.

EXAMPLE 8

Preparation of Delayed Release Tablets

A coating formulation is prepared using the components of Table 2:

TABLE 2

| COMPONENT | AMOUNT w/w % | PREFERRED AMOUNT w/w % |
|---|---|---|
| Eudragit ® RS 30D | 30–60 | 35–50 |
| Eudragit ® RL 30D | 0–10 | 0.5–5 |
| Talc | 5–20 | 5–15 |
| Acetyl t-butyl citrate | 1–10 | 2–6 |
| Simethicone emulsion | 0.01–0.05 | 0.01–0.03 |
| Water | 40–70 | 50–60 |

A stainless steel vessel is charged with 50 kg of water and 6 kg of talc. The mixture is then mixed to form a suspension. A second vessel is charged with 40 kg of Eudragit® RS 30D and 0.02 kg of simethicone emulsion. The mixture is slowly agitated. While agitating, 2 kg of Eudragit® RL 30D and 2.5 kg of acetyltributyl citrate are added and mixed until uniform. The talc suspension is added to the second vessel and stirred to form the polymeric coating formulation. A conventional coating pan or a fluidized bed coater is then charged with 10 kg of tablets as prepared in Example 2 and coated with 3 to 15 kg of the polymeric coating formulation described above until the desired dissolution profile is obtained. Talc may be used to dust the tablets during the polymeric coating. The coated tablets are dried to remove solvent.

EXAMPLE 9

Preparation of Delayed Release Beads

A conventional coating pan or a fluidized bed coater is charged with 10 kg of the immediate release beads as prepared in Example 3, 4, 5, 6 or 7 and coated with 5 to 20 kg of the polymeric coating solution as prepared in Example 8 until the desired dissolution profile is obtained. Talc may be used to dust the tablets during the polymeric coating. The coated beads are dried to remove solvent.

EXAMPLE 10

Preparation of Delayed Release Tablets

A coating formulation is prepared using the components of Table 3:

TABLE 3

| COMPONENT | AMOUNT w/w % | PREFERRED AMOUNT w/w % |
|---|---|---|
| Eudragit ® S100 | 1–5 | 2–4 |
| Ethylcellulose | 2–10 | 3–6 |
| Talc | 3–10 | 4–7 |
| Dibutyl phthalate | 0.1–0.5 | 0.1–0.3 |
| Simethicone emulsion | 0.01–0.03 | 0.01–0.02 |
| Isopropanol | 40–70 | 50–60 |
| Acetone | 20–40 | 25–35 |
| Optional Pigment | 20–40 | 25–35 |

A stainless steel vessel is charged with 20 kg of isopropanol. Eudragit® S (3 kg) is added slowly to the solution with agitation until the Eudragit® S is completely dissolved. Dibutyl phthalate (0.3 kg) is added and dissolved in the mixture by mixing. In a separate vessel, talc (7 kg) is added into a mixture of 48 kg of isopropanol and 48 kg of acetone and stirred to form a uniform suspension. Ethylcellulose (5 kg) is added slowly to the talc suspension and the mixture is agitated to dissolve the ethylcellulose. The talc/ethylcellulose suspension is added to the Eudragit® S solution and the mixture is agitated to form a uniform suspension. A conventional coating pan or a fluidized bed coater is then charged with 10 kg of tablets as prepared in Example 2 and coated with 10 to 30 kg of the polymeric coating solution as described above until the desired dissolution profile is obtained. Talc may be used to dust the tablets during coating. The coated tablets are dried to remove solvents.

EXAMPLE 11

Preparation of Delayed Release Beads

A conventional coating pan or a fluidized bed coater is charged with 10 kg of beads prepared in Example 3, 4, 5, 6 or 7. The beads are coated with 15 to 40 kg of the polymeric coating solution described in Example 10 until the desired dissolution profile is obtained. The coated beads are dried to remove solvents.

EXAMPLE 12

Preparation of Delayed Release Tablets

A coating formulation is prepared using the components of Table 4:

TABLE 4

| COMPONENT | AMOUNT w/w % | PREFERRED AMOUNT w/w % |
|---|---|---|
| Eudragit ® S100 | 3–15 | 5–10 |
| Talc | 1–5 | 1–4 |
| Dibutyl phthalate | 0.3–4.0 | 0.7–2.0 |
| Isopropanol | 60–95 | 70–90 |

A stainless steel vessel is charged with 77 kg of isopropanol. Eudragit® S 100 (11 kg) is added slowly to the solution with agitation the until the Eudragit® S 100 is completely dissolved. Dibutyl phthalate (2.2 kg) is added and dissolved in the mixture by mixing. In a separate vessel, talc (2.7 kg) is added into 57 kg of isopropanol and stirred to form a uniform suspension. The talc suspension is added to the Eudragit® S solution and the mixture is agitated to form a uniform suspension. A conventional coating pan or a fluidized bed coater is then charged with 10 kg of tablets as prepared in Example 2 and coated with 5 to 10 kg of the polymeric coating solution described above until the desired dissolution profile is obtained. The coated tablets are dried to remove solvents.

EXAMPLE 13

Preparation of Delayed Release Beads

A conventional coating pan or a fluidized bed coater is charged with 10 kg of beads as prepared in Example 3, 4, 5, 6 or 7 and coated with 10 to 15 kg of the polymeric coating solution described in Example 12 until the desired dissolution profile is obtained. The coated beads are then dried to remove solvents.

EXAMPLE 14

Preparation of Delayed Release Tablets

A coating formulation is prepared using the components of Table 5:

TABLE 5

| COMPONENT | AMOUNT w/w % | PREFERRED AMOUNT w/w % |
|---|---|---|
| Eudragit ® S100 | 5–25 | 10–20 |
| Triethyl citrate | 3–12 | 5–10 |
| Glyceryl monostearate | 0.1–2.0 | 0.2–0.8 |
| Ammonium solution 1 N | 2–12 | 5–10 |
| Optional Pigment | 0.2–5.0 | 0.4–4.0 |
| Simethicone emulsion | 0.005–0.05 | 0.01–0.04 |
| Water | 50–90 | 60–80 |

A stainless steel vessel is charged with 70 kg of water. Eudragit® S 100 (14.4 kg) is added slowly to the solution with agitation until dispersed. Approximately 7.2 kg of a 1N ammonium solution is added slowly to neutralize the polymer. Triethyl citrate (7.2 kg) and 0.4 kg of glyceryl monostearate is then added to the solution and the mixture is agitated to dissolve. A conventional coating pan or a fluidized bed coater is then charged with 10 kg of tablets as prepared in Example 2 and coated with 5 to 15 kg of the polymeric coating solution as described above until the desired dissolution profile is obtained. Talc may be used during the coating process to reduce tackiness. The coated tablets are dried to remove solvents.

EXAMPLE 15

Preparation of Delayed Release Beads

A conventional coating pan or a fluidized bed coater is charged with 10 kg of beads prepared in Example 3, 4, 5 6 or 7 and coated with 10 to 25 kg of the polymeric coating solution described in Example 14 until the desired dissolution profile is obtained. The coated beads are dried to remove solvents.

EXAMPLE 16

Preparation of a Delayed Release Tablet

A coating formulation is prepared using the components of Table 6:

TABLE 6

| COMPONENT | AMOUNT w/w % | PREFERRED AMOUNT w/w % |
|---|---|---|
| Eudragit ® RS 12.5%* | 20–60 | 30–50 |
| Eudragit ® RL 12.5%* | 2–20 | 3–15 |
| Isopropanol | 30–70 | 40–60 |

*Products are prepared in acetone/isopropanol/water mixture (39:58:3)

A stainless steel vessel is charged with 50 kg of isopropanol. Eudragit® RS 12.5% (45 kg) and Eudragit® RL 12.5% (5 kg) are added slowly to the solution with agitation. A conventional coating pan or a fluidized bed coater is then charged with 10 kg of tablets as prepared in Example 2 and coated with 5 to 20 kg of the polymeric coating solution described above until the desired dissolution profile is obtained. Talc or magnesium stearate may be used during the coating process to reduce tackiness. The coated tablets are dried to remove solvents.

EXAMPLE 17

Preparation of Delayed Release Beads

A conventional coating pan or a fluidized bed coater is charged with 10 kg of beads prepared in Example 3, 4, 5, 6 or 7 and coated with 10 to 30 kg of the polymeric coating solution described in Example 16. The coated beads are then dried to remove solvents.

EXAMPLE 18

Preparation of a Delayed Release Tablet

A coating formulation is prepared using the components of Table 7:

TABLE 7

| COMPONENT | AMOUNT w/w % | PREFERRED AMOUNT w/w % |
|---|---|---|
| Ethylcellulose | 2–40 | 4–30 |
| Polyvinylpyrrolidone | 0.2–3 | 0.3–1 |
| Isopropanol | 60–97 | 70–95 |

A stainless steel vessel is charged with 94.5 kg of isopropanol. Ethylcellulose (5 kg) is added with slow agitation until the ethylcellulose is completely to dissolved. Polyvinylpyrrolidone (0.5 kg) is added and the mixture is agitated slowly until all the polyvinylpyrrolidone is completely dissolved. A conventional coating pan or a fluidized bed coater is then charged with 10 kg of tablets as prepared in Example 2 and coated with 5 to 20 kg of the polymeric coating solution described above. Talc may be used during the coating process to reduce tackiness. The coated tablets are dried to remove solvents. The coated tablets may be further coated with coating a solution as described in Example 8, 10, 12, 14 or 16 (see also Table 2, 3, 4, 5 or 6) to obtain the desired dissolution profile.

EXAMPLE 19

Preparation of Delayed Release Beads

A conventional coating pan or a fluidized bed coater is charged with 10 kg of beads prepared in Example 3, 4, 5, 6 or 7 and coated with 10 to 30 kg of the polymeric coating solution as described in Example 18. The coated beads are dried to remove solvents. The coated beads are further coated with coating a solution as described in Example 8, 10, 12, 14 or 16 (see also Table 2, 3, 4, 5 or 6) to obtain the desired dissolution profile.

EXAMPLE 20

Preparation of Delayed Release Tablets

A coating formulation is prepared using the components of Table 8:

TABLE 8

| COMPONENT | AMOUNT w/w % | PREFERRED AMOUNT w/w % |
|---|---|---|
| Hydroxypropyl methylcellulose | 2–10 | 3–6 |
| Polyethylene glycol | 0.1–1.0 | 0.2–0.5 |
| Ethanol, water, or mixture thereof | 85–98 | 93–97 |

A stainless steel vessel is charged with 95.5 kg of ethanol or water. Hydroxypropyl methylcellulose (4 kg) and 0.5 kg polyethylene glycol are added slowly to the mixture with slow agitation. A conventional coating pan or a fluidized bed coater is then charged with 10 kg of tablets as prepared in Example 2 and coated with 10–20 kg of the polymeric coating solution described above. Talc may be used during the coating process to reduce tackiness. The coated tablets are dried to remove solvents. The coated tablets may be further coated with a coating solution as described in Example 8, 10, 12, 14, 16 or 18 (see also Table 2, 3, 4, 5, 6 or 7) to obtain the desired dissolution profile.

EXAMPLE 21

Preparation of Delayed Release Beads

A conventional coating pan or a fluidized bed coater is charged with 10 kg of beads prepared in Example 3, 4, 5, 6 or 7 and coated with 10 to 35 kg of polymeric coating solution as described in Example 20 (see also Table 8). The coated beads are dried to remove solvents. The coated beads are further coated with a coating solution as described in Example 8, 10, 12, 14, 16 or 18 (see also Table 2, 3, 4, 5, 6 or 7) to obtain the desired dissolution profile.

EXAMPLE 22

Preparation of Delayed Release Tablets

A coating formulation is prepared using the components of Table 9:

TABLE 9

| COMPONENT | AMOUNT w/w % | PREFERRED AMOUNT w/w % |
|---|---|---|
| Aquacoat ® ECD* | 60–90 | 70–85 |
| Dibutyl sebacate | 3–10 | 4–8 |
| Water | 5–40 | 10–30 |

*An ethylcellulose 30% solid dispersion manufactured by FMC.

A stainless steel vessel is charged with 7.8 kg of Aquacoat® ECD. Dibutyl sebacate (0.6 kg) and 1.6 kg of water are added and the mixture is stirred for at least 30 minutes. A conventional coating pan or a fluidized bed coater is then charged with 10 kg of tablets as prepared in Example 2 and coated with 1.5–5 kg of the polymeric coating solution described above. Talc may be used during the coating process to reduce tackiness. The coated tablets are dried to remove solvents. The coated tablets may be further coated with a coating solution as described in Example 8, 10, 12, 14 or 16 (see also Table 2, 3, 4, 5 or 6) to obtain the desired dissolution profile.

EXAMPLE 23

Preparation of Delayed Release Beads

A conventional coating pan or a fluidized bed coater is charged with 10 kg of beads prepared in Example 3, 4, 5, 6 or 7 and coated with 3 to 10 kg of polymeric coating solution as described in Example 22 (see also Table 9). The coated beads are dried to remove solvents. The coated beads may be further coated with a coating solution as described in Example 8, 10, 12, 14 or 16 (see also Table 2, 3, 4, 5 or 6) to obtain the desired dissolution profile.

EXAMPLE 24

Preparation of a Delayed Release Tablets

A conventional coating pan or a fluidized bed coater is charged with 10 kg of tablets as prepared in Example 2 and coated with amylose-Ethocel® (1:4 w/w) (Colorcon®) until a coat weight gain of 10–30% is achieved. The coated tablets are further coated with a coating solution as described in Example 8, 10, 12, 14, 16, 18 or 22 (see also Table 2, 3, 4, 5, 6, 7 or 9) to obtain the desired dissolution profile.

EXAMPLE 25

Preparation of Delayed Release Beads

A conventional coating pan or a fluidized bed coater is charged with 10 kg of beads prepared in Example 3, 4, 5, 6 or 7 and coated with amylose-Ethocel® (1:4 w/w) (Colorcon®) until a coat weight gain of 15–50% is achieved. The coated beads are further coated with a coating solution as described in Example 8, 10, 12, 14, 16, 18 or 22 (see also Table 2, 3, 4, 5, 6, 7 or 9) to obtain the desired dissolution profile.

EXAMPLE 26

Preparation of Delayed Release Tablets

A conventional coating pan or a fluidized bed coater is charged with 10 kg of tablets as prepared in Example 2 and coated with a 2–4% pectin solution until the coating weight gain is 10–25%. The pectin-coated tablets are further coated with a coating solution as described in Example 8, 10, 12, 14, 16, 18 or 22 (see also Table 2, 3, 4, 5, 6, 7 or 9) to obtain the desired dissolution profile.

EXAMPLE 27

Preparation of Delayed Release Beads

A conventional coating pan or a fluidized bed coater is charged with 10 kg of beads prepared in Example 3, 4, 5, 6 or 7 and coated with a 2–4% pectin solution until the coating weight gain is 15–50%. The pectin-coated beads are further coated with a coating solution as described in Example 8, 10, 12, 14, 16, 18 or 22 (see also Tables 2, 3, 4, 5, 6, 7 or 9) to obtain the desired dissolution profile.

EXAMPLE 28

Preparation of a Final Dosage Form of Sotalol

The final dosage form for sotalol pulsatile delivery units are prepared by mixing the rapid release and the appropriate delayed release populations together in predetermined proportions and filling the capsules with the mixture or a further blend with excipients and compressed into tablets.

Each sotalol once-a-day delivery unit contains 50 to 700 mg sotalol hydrochloride divided evenly between each of the pulses in the dosage form.

Several forms of pulsatile delivery units are possible based on different combinations of the various drug-containing populations. Representative examples of these dosage forms are provided below.

(1) Encapsulation of the rapid release granules from Example 1 and the delayed release beads of Example 9, 11, 13, 15, 17, 19, 21, 23, 25 or 27.
(2) Encapsulation of the rapid release beads obtained from Example 3, 4, 5, 6 or 7 and the delayed release beads obtained from Example 9, 11, 13, 15, 17, 19, 21, 23, 25 or 27.
(3) Encapsulation of the rapid release tablets obtained from Example 2 and the delayed release tablets obtained from Example 8, 10, 12, 14, 16, 18, 20, 22, 24 or 26.
(4) Encapsulation of the rapid release granules obtained from Example 1 and the delayed release tablet obtained from Example 8, 10, 12, 14, 16, 18, 20, 22, 24 or 26.
(5) Encapsulation of the rapid release beads obtained from Example 3, 4, 5, 6 or 7 and the delayed release tablet obtained from one of Examples 8, 10, 12, 14, 16, 18, 20, 22, 24 or 26.
(6) Encapsulation of the rapid release tablet obtained from Example 2 and the delayed release beads obtained from Example 9, 11, 13, 15, 17, 19, 21, 23, 25 or 27.
(7) Compression of rapid release granules obtained from Example 1 and the delayed release beads obtained from Example 9, 11, 13, 15, 17, 19, 21, 23, 25 or 27 with the addition of excipients such as lactose, microcrystalline cellulose and lubricants.
(8) Compression of rapid release beads obtained from Example 3, 4, 5, 6 or 7 and the delayed release beads obtained from Example 9, 11, 13, 15, 17, 19, 21, 23, 25 or 27 with the addition of excipients such as lactose, microcrystalline cellulose and a lubricant.
(9) Compression coat of the delayed release tablet from Example 8, 10, 12, 14, 16, 18, 20, 22, 24 or 26 with the granulation of Example 1, which is further diluted with excipients such as lactose, microcrystalline cellulose and a lubricant.
(10) Coating of the delayed release tablet from Example 8, 10, 12, 14, 16, 18, 20, 22, 24 or 26 with a coating solution prepared with sotalol as described in example 3 or 4 until the desired amount of sotalol is applied. The coated tablets may be further encapsulated to provide the desired dose.

(11) Coating of the delayed release beads from Examples 9, 11, 13, 15, 17, 19, 21, 23, 25 or 27 with a coating solution prepared with sotalol as described in example 3 or 4, until the desired amount of sotalol is applied. The coated beads may be further encapsulated to provide the desired dose.

In addition, the immediate release tablets and/or the delayed release tablets may be divided into two or more tablets, such that, for example, 320 mg of sotalol is divided into two 120-mg or four 80-mg immediate release tablets and/or into two 120-mg or four 80-mg delayed release tablets.

EXAMPLE 29

Dosage Form Providing Two Pulses of Amiodarone Hydrochloride

Immediate release tablets are prepared according to Example 2 except that amiodarone hydrochloride is substituted for sotalol hydrochloride and the subsequent tablet contains 200 mg of amiodarone hydrochloride. Delayed release tablets are prepared according to Example 8 except that amiodarone hydrochloride is substituted for sotalol hydrochloride and the subsequent tablet contains 200 mg of amiodarone hydrochloride. An immediate release tablet and delayed release tablet are placed in a capsule and the capsule is sealed. Upon administration, the dosage form provides pulsatile delivery of amiodarone hydrochloride. This example may be repeated using amiodarone delayed release tablets prepared according to any of Examples 10, 12, 14, 16, 18, 22 and 26.

Alternatively, the immediate release tablets and/or the delayed release tablets may be divided into two or more tablets, such that the 200 mg of amiodarone hydrochloride is divided into two 100-mg or four 50-mg immediate release tablets and/or into two 100-mg or four 50-mg delayed release tablets.

EXAMPLE 30

A typical batch of sotalol hydrochloride tablet, 40 mg, was prepared and coated with a delayed released polymeric solution. Formulation for the delayed released sotalol hydrochloride tablets is provided in Table 10 and the drug release profiles associated with coated weight gain are provided in Table 11.

TABLE 10

| INGREDIENTS | WEIGHT mg/tablet | % W/W |
|---|---|---|
| TABLET CORE: | | |
| Sotalol hydrochloride | 40.0 | 74.6 |
| Prosolv ®* | 8.0 | 14.9 |
| Starch 1500 | 5.36 | 10.0 |
| Magnesium Stearate | 0.27 | 0.5 |
| Core weight | 53.63 | |
| DELAYED RELEASE COATING: | COATED WEIGHT GAIN, mg | % WEIGHT GAIN |
| Eudragit ® S100 | 3.2–13.5 | 6.0–25.2 |
| Triethyl citrate | 1.6–6.8 | 3.0–12.7 |

TABLE 10-continued

| Talc | 0.8–3.4 | 1.49–6.3 |
|---|---|---|
| Ammonium hydroxide | 0.058–0.24 | 0.11–0.45 |

*Prosolv ® is trade name of Penwest product it contains microcrystalline cellulose and colloidal silica.

The sotalol core tablets were prepared using conventional manufacturing techniques known to those skilled in the art. Briefly, the sotalol core tablets were prepared by blending the active ingredient, Prosolv® and starch in a container. The blend was granulated with purified water and dried. The dried granulation was milled to desired particle size and compressed using a 5/32" diameter tooling. The cores were coated with an aqueous coating solution containing 16.55% w/w Eudragit® S100, 8.42% w/w ammonium solution (3.5% ammonium hydroxide), 8.27% w/w triethyl citrate and 5.4% w/w Talc using a fluid bed coating apparatus equipped with a Wurster column.

In vitro drug release studies for the coated delayed release Sotalol tablets were conducted on tablets with different coated weights using USP dissolution apparatus II (paddles) at 50 rpm. Drug release studies were conducted in dissolution media (37+/−0.5 C.) of:

| Condition (1): | |
|---|---|
| Hour 0–2: | 900 ml 0.1N hydrochloric acid |
| Hour 2–4: | 900 ml phosphate buffer pH 6.8 |
| >Hour 4 | 900 ml phosphate buffer, pH 7.0 |
| Condition (2): | |
| Hour 0–2: | 900 ml 0.1N hydrochloric acid |
| Hour 2–4: | 900 ml phosphate buffer pH 6.8 |
| >Hour 4 | 900 ml phosphate buffer, pH 7.2 |
| Condition (3): | |
| Hour 0–2: | 900 ml 0.1N hydrochloric acid |
| Hour 2–4: | 900 ml phosphate buffer pH 6.8 |
| Hour 4–6: | 900 ml phosphate buffer pH 7.0 |
| >Hour 6: | 900 ml phosphate buffer, pH 7.2 |

In vitro drug release study results indicated that the sotalol delayed release tablets prepared according to the formulation described in Table 10 resisted drug release for 2 hours in acid and 2 hours in a medium adjusted to a pH 6.8 through a buffer. The drug started to release hours after the dissolution medium was switched to a phosphate buffer of pH 7.0 or higher (Conditions (1) or (2) or (3)). The drug dumping time associated with the corresponding coated weight gain (and % coated weight gain) for tablets are provided in Table 1. The delayed release tablets are able to protect the sotalol from releasing for at least 7 to 17 hours depending on the coated weight and pH of the dissolution medium.

TABLE 11

Drug Release Profile and Drug Dumping Time for Sotalol Hydrochloride Delayed Release Tablets.

| TABLET # | COATED WEIGHT GAIN mg | % COATED WEIGHT GAIN** | DISSOLUTION CONDITION (1) or (2) or (3) | % DRUG RELEASE IN ACID HOUR 0–2 | % DRUG RELEASE in PH 6.8 HOUR 2–4 | DRUG DUMPING TIME* in PH 7.0 or HIGHER |
|---|---|---|---|---|---|---|
| 1 | 6.6 | 12.3 | (1) | NS | NS | 8 |
| 2 | 14.5 | 27.0 | (1) | NS | NS | 11 |
| 3 | 18.6 | 35.7 | (1) | NS | NS | 11 |
| 4 | 18.5 | 34.5 | (2) | NS | NS | 7–8 |
| 5 | 19.3 | 36.0 | (2) | NS | NS | 8 |
| 6 | 19.2 | 35.8 | (1) | NS | NS | 15–17 |
| 7 | 16.3 | 30.4 | (1) | NS | NS | 15 |
| 8 | 19.2 | 35.8 | (3) | NS | NS | 10–11 |
| 9 | 22.8 | 42.5 | (3) | NS | NS | 11 |
| 10 | 11.7 | 21.8 | (3) | NS | NS | 9 |

NS: No significant drug release.
*Drug dumping time was measured starting 0 time dissolution in acidic medium.
**Based on a core tablet weight of 53.6 mg

EXAMPLE 31

Placebo tablets (approximately 150 mg) were coated with an acidic coating solution containing approximately 0.96% pectin and 0.33% chitosan. The disintegration time of the coated tablets was studied using the USP apparatus II (paddles at 50 rpm in a pH 6.3 phosphate buffer). A coat weight gain of approximately 3.5% delayed the disintegration time for approximately 2 to 4 hours. This type of coating may be applied in addition to the Eudragit® S coating as provided in Example 30 to obtain a desired drug delivery to the targeted site.

EXAMPLE 32

Placebo tablets (approximately 150 mg) were coated with an acidic coating solution containing approximately 1.3% pectin and 0.7% Eudragit E. The disintegration time of the coated tablets was studied using the USP apparatus II (paddles at 50 rpm in a pH 6.3 phosphate buffer). A coat weight gain of approximately 9% delayed the disintegration time for approximately 30 minutes. This type of coating may be applied in addition to the Eudragit S coating as provided in Example 31 to obtain a desired drug delivery to the targeted site.

We claim:

1. A pulsatile release dosage form for treatment of conditions responsive to the administration of an antiarrhythmic agent, comprising:
   (a) an immediate release dosage unit comprising a first dose of the active agent that is released substantially immediately following oral administration of the dosage form to a patient, said first dose providing an initial burst of active agent followed by a time interval during which little or no active agent is released from the immediate release dosage unit;
   (b) a delayed release dosage unit comprising a second dose of the active agent and a means for delaying release of the second dose until approximately 6 hours to less than 14 hours following oral administration of the dosage form; and optionally
   (c) a second delayed release dosage unit comprising a third dose of the active agent and a means for delaying release of the third dose until at least 4 hours to approximately 8 hours following release of the second dose from the dosage form.

2. The dosage form of claim 1, wherein all of the dosage units are housed in a closed capsule.

3. The dosage form of claim 2, wherein each dosage unit comprises a drug-containing compressed tablet.

4. The dosage form of claim 3, wherein each dosage unit comprises a plurality of compressed tablets.

5. The dosage form of claim 2, wherein each dosage unit comprises a plurality of drug-containing beads.

6. The dosage form of claim 2, wherein each dosage unit comprises a plurality of drug-containing granules.

7. The dosage form of claim 2, wherein the immediate release dosage unit comprises a plurality of drug-containing particles.

8. The dosage form of claim 1, wherein the dosage units are comprised of drug-containing beads, granules or particles compressed in a single tablet.

9. The dosage form of claim 1, wherein the dosage units are comprised of drug-containing beads or granules that represent integral and discrete segments of a single tablet.

10. The dosage form of claim 9, wherein the integral and discrete segments are layers or successive compression coatings.

11. The dosage form of claim 1, wherein the optional third dosage unit is not present.

12. The dosage form of claim 11, wherein the second dose is released approximately 8 hours to less than 14 hours following oral administration.

13. The dosage form of claim 12, wherein the second dose is released approximately 10 hours to 12 hours following oral administration.

14. The dosage form of claim 11, wherein the immediate release dosage unit comprises an outer layer surrounding an inner core, said inner core comprising the delayed release dosage unit.

15. The dosage form of claim 11, wherein the immediate release dosage unit comprises an outer layer and the delayed release dosage comprises an inner layer surrounding an inner core containing the active agent.

16. The dosage form of claim 11, wherein each dosage unit contains approximately 30 wt. % to 70 wt. % of the total active agent in the dosage form.

17. The dosage form of claim 16, wherein each dosage unit contains approximately 40 wt. % to 60 wt. % of the total active agent in the dosage form.

18. The dosage form of claim 11, wherein the first and second doses are approximately equal.

19. The dosage form of claim 1, wherein the optional third dosage unit is present.

20. The dosage form of claim 19, wherein the second dose is released approximately 6 hours to 10 hours following oral administration.

21. The dosage form of claim 20, wherein the second dose is released approximately 7 hours to 9 hours following oral administration.

22. The dosage form of claim 19, wherein the third dose is released approximately 14 hours to 18 hours following oral administration.

23. The dosage form of claim 19, wherein each dosage unit contains approximately 25 wt. % to 40 wt. % of the total active agent in the dosage form.

24. The dosage form of claim 19, wherein the first, second and third doses are approximately equal.

25. The dosage form of claim 19, wherein the immediate release dosage unit comprises an outer layer, and the delayed release dosage unit comprises an intermediate layer thereunder surrounding an inner core comprising the second delayed release dosage unit.

26. The dosage form of claim 19, wherein the immediate release dosage unit comprises an outer layer containing the active agent and an intermediate coating thereunder surrounds a core comprised of immediate release beads or granules and delayed release beads or granules, wherein the immediate release beads or granules represent a second dose, and the delayed release beads or granules represent a third dose.

27. The dosage form of claim 1, for once daily dosing.

28. The dosage form of claim 1, wherein the active agent has Class II or Class III antiarrhythmic activity.

29. The dosage form of claim 28, wherein the active agent has Class II antiarrhythmic activity.

30. The dosage form of claim 28, wherein the active agent has Class III antiarrhythmic activity.

31. The dosage form of claim 1, wherein the active agent is selected from the group consisting of d,l-sotalol, d-sotalol, l-sotalol, amiodarone, dofetilide, azimilide, cibenzoline, bunafitidine, and pharmacologically acceptable salts thereof.

32. The dosage form of claim 31, wherein the active agent is d,l-sotalol, d-sotalol, l-sotalol, a pharmacologically acceptable salt thereof, or mixtures of any of the foregoing.

33. The dosage form of claim 32, wherein the active agent is d,l-sotalol hydrochloride, d-sotalol hydrochloride, l-sotalol hydrochloride or a mixture thereof.

34. The dosage form of claim 33, wherein the total amount of active agent contained in the immediate release, delayed release and optional second delayed release dosage units is in the range of approximately 50 to 700 mg.

35. The dosage form of claim 34, wherein the total amount of active agent contained in the immediate release, delayed release and optional second delayed release dosage units is in the range of approximately 80 mg to 640 mg.

36. The dosage form of claim 31, wherein the active agent is amiodarone or a pharmacologically acceptable salt thereof.

37. The dosage form of claim 36, wherein the active agent is amiodarone hydrochloride.

38. The dosage form of claim 37, wherein the total amount of amiodarone contained in the immediate release, delayed release and optional second delayed release dosage units is in the range of approximately 600 mg to 800 mg.

39. The dosage form of claim 31, wherein the active agent is dofetilide.

40. The dosage form of claim 39, wherein the total amount of dofetilide contained in the immediate release, delayed release and optional second delayed release dosage units is in the range of approximately 10 $\mu$g to 10 mg.

41. The dosage form of claim 40, wherein the total amount of dofetilide contained in the immediate release, delayed release and optional second delayed release dosage units is in the range of approximately 200 $\mu$g to 1000 $\mu$g.

42. The dosage form of claim 41, wherein the immediate release dosage unit and delayed release dosage unit each contains approximately 100 $\mu$g to 500 $\mu$g of dofetilide and the optional second delayed release dosage unit is not present.

43. The dosage form of claim 1, wherein the means for delaying release comprises at least one coating of a delayed release polymeric material.

44. The dosage form of claim 43, comprising two or more coatings of a delayed release polymeric material.

45. The dosage form of claim 1, wherein the means for delaying release comprises a matrix of a delayed release polymeric material.

46. The dosage form of any one of claims 43, 44 or 45, wherein the polymeric material is comprised of bioerodible, hydrolyzable, enzymatically degradable and/or gradually water-soluble polymer.

47. The dosage form of claim 46, wherein the polymeric material is selected from the group consisting of cellulosic polymers, acrylic acid polymers and copolymers, vinyl polymers, enzymatically degradable polymers, shellac and combinations thereof.

48. The dosage form of claim 47, wherein the polymeric material is comprised of a cellulosic polymer.

49. The dosage form of claim 48, wherein the cellulosic polymer is selected from the group consisting of hydroxypropylcellulose, hydroxyethyl cellulose, hydroxymethyl cellulose, hydroxypropyl methylcellulose, hydroxypropyl methylcellulose acetate succinate, hydroxypropyl methylcellulose phthalate, methylcellulose, ethylcellulose, cellulose acetate, cellulose acetate phthalate, cellulose acetate trimellitate, sodium carboxymethylcellulose, and combinations thereof.

50. The dosage form of claim 47, wherein the polymeric material is comprised of an acrylic acid polymer or copolymer.

51. The dosage form of claim 50, wherein the polymeric material is a methacrylic resin copolymer comprised of acrylic acid, methacrylic acid, methyl acrylate, ethyl acrylate, methyl methacrylate, ethyl methacrylate and combinations thereof.

52. The dosage form of claim 47, wherein the polymeric material is comprised of a vinyl polymer or copolymer.

53. The dosage form of claim 52, wherein the polymeric material is selected from the group consisting of polyvinyl pyrrolidone, polyvinyl acetate, polyvinyl acetate phthalate, polyvinyl acetate crotonic acid copolymer, ethylene-vinyl acetate copolymer and combinations thereof.

54. The dosage form of claim 47, wherein the polymeric material is comprised of an enzymatically degradable polymer.

55. The dosage form of claim 54, wherein the enzymatically degradable polymer is selected from the group consisting of azo polymers, pectin, chitosan, amylose, guar gum, zein, and combinations thereof.

56. The dosage form of claim 1, wherein at least one of the immediate release, delayed release and optional second delayed release dosage units further comprises a diluent.

57. The dosage form of claim of claim 1, wherein at least one of the immediate release, delayed release and optional second delayed release dosage units comprises a lubricant.

58. The dosage form of claim 1, wherein at least one of the immediate release, delayed release and optional second delayed release dosage units comprises a disintegrant.

59. The dosage form of claim 1, wherein at least one of the immediate release, delayed release and optional second delayed release dosage units comprises a binder.

60. The dosage form of claim 1, wherein at least one of the immediate release, delayed release and optional second delayed release dosage units comprises a colorant.

61. A method for treating an individual suffering from documented ventricular arrhythmia comprising administering the dosage form of claim 1 to the individual once daily to minimize the development of tolerance due to supersensitization of the cardioreceptors.

62. A method for treating an individual suffering from sustained ventricular tachycardia comprising administering to the individual, once-a-day, the dosage form of claim 1.

63. A method for treating an individual suffering from ventricular tachycardia administering the dosage form of claim 1 to the individual once daily to minimize the development of tolerance and thereby loss of efficacy due to supersensitization of the cardioreceptors.

64. A method for treating an individual suffering from atrial fibrillation, atrial flutter, or supra ventricular arrhythmia, comprising administering the dosage form of claim 1 to the individual once daily.

* * * * *